United States Patent [19]

Cioca et al.

[11] Patent Number: 4,497,862
[45] Date of Patent: Feb. 5, 1985

[54] MOISTURE VAPOR PERMEABLE SHEET MATERIALS

[75] Inventors: George Cioca, Coatesville; George F. Feeley, Downington, both of Pa.; Joseph B. Brabson, Wilmington, Del.; Peter Barth, Neuwied, Fed. Rep. of Germany

[73] Assignee: Seton Company, Newark, N.J.

[21] Appl. No.: 521,147

[22] Filed: Aug. 8, 1983

Related U.S. Application Data

[62] Division of Ser. No. 314,536, Oct. 26, 1981, Pat. No. 4,415,628.

[51] Int. Cl.³ .......................... B32B 27/34; B32B 27/40
[52] U.S. Cl. .................................. 428/220; 260/123.7; 428/423.1; 428/478.2; 521/50; 524/27
[58] Field of Search ...................... 428/343, 220, 423.1; 428/428.2; 260/123.7; 524/27; 521/50

[56] References Cited

U.S. PATENT DOCUMENTS

| 4,285,986 | 8/1981 | Cioca et al. | 260/123.7 X |
| 4,295,894 | 10/1981 | Cioca et al. | 260/123.7 X |
| 4,307,717 | 12/1981 | Hymes et al. | 428/343 X |
| 4,363,760 | 12/1982 | Cioca | 260/123.7 |
| 4,412,947 | 11/1983 | Cioca | 260/123.7 |

Primary Examiner—Thomas J. Herbert
Attorney, Agent, or Firm—Webb, Burden, Robinson & Webb

[57] ABSTRACT

A moisture vapor permeable sheet material is comprised of a homogeneous admixture of a synthetic polymer material and a protein derivative. The sheet material is moisture vapor permeable and non-penetrable by liquid water. The sheet material additionally can have coated thereon a pressure sensitive adhesive which is comprised of a snythetic organic polymer adhesive and a soluble protein derivative in solid solution. Sheet material is formed by providing a homogeneous fluid solution of a soluble protein derivative and a synthetic organic polymer in a solvent. The protein derivative has a pH level compatible with the pH level of the organic polymer. Film is formed from the homogeneous fluid solution and the solvent is removed from the film to form the sheet material which is moisture vapor permeable. When the sheet material includes an adhesive, the adhesive is coated as a fluid solution in a solvent on one side of the sheet material.

19 Claims, No Drawings

MOISTURE VAPOR PERMEABLE SHEET MATERIALS

This application is a division of application Ser. No. 314,536, filed Oct. 26, 1981, now U.S. Pat. No. 4,415,628.

BACKGROUND OF THE INVENTION

This invention relates to moisture vapor permeable dressings used in surgical and general medical applications such as bandaging and the like.

It is well recognized in the field of bandaging, wound healing, surgical incise drapes and similar sheet materials that in promoting healing processes the wound dressing or bandage should have characteristics closely resembling skin. One such characteristic is moisture vapor permeability which defines a condition wherein the dressing or the like will transmit water vapor therethrough so that maceration of the wound does not occur. On the other hand, the dressing should be sufficiently continuous in order to prevent the entrance of bacteria into the wound which may cause infection.

Moisture vapor permeability can be provided to wound dressings, surgical drapes and the like by two separate routes. One such route is by providing a microporous structure as the bandaging material or wound dressing, which pores allow moisture vapor to pass therethrough from the wound and into the atmosphere. The degree of microporosity, particularly the size of the pores, is particularly important since if the pores are too large, liquid water and bacteria may penetrate through the structure into the wound, thus increasing the risk of infection. When the micropores are sufficiently small, the desirable result is that moisture vapor will pass through the micropores from the wound, but bacteria and liquid water cannot pass through the micropores from the dressing surface into the wound.

Another means of providing moisture vapor permeability to a dressing is by having the dressing constructed of a material which is continuous, i.e. nonmicroporous which passes water vapor at a molecular level from molecular chain to molecular chain. This type of moisture vapor permeability is the desired type of moisture vapor permeability since it eliminates regulation of pore size to prevent entrance of bacteria and liquid water into the wound. Such moisture vapor permeability without micropores is alluded to in U.S. Pat. No. 3,645,835. However, one of the drawbacks of continuous moisture vapor permeable dressings is that although they have moisture vapor permeability, they do not have sufficient moisture vapor permeability, i.e., approaching that of human skin, to be completely effective in preventing maceration of the wound.

True moisture vapor permeability is provided by a dressing which acts as a membrane through which moisture will pass at a specific rate and, therefore, the moisture vapor transmission rate of the dressing is not contingent upon the thickness of the dressing.

Although moisture vapor permeable dressings have been made which are microporous such as disclosed in U.S. Pat. No. 3,121,021 with high moisture vapor permeability, there has been great difficulty in providing a dressing with high moisture vapor permeability i.e. over 300 and preferably over 500 g/m$^2$/24 hours at 40° C. which is nonmicroporous, i.e. continuous.

In addition, in the most desired instance the dressing is composed of some type of polymeric sheet material with an adhesive on one side by which the dressing will adhere to the skin. Thus, if a dressing is to be continuous rather than microporous in all instances, the sheet material and the adhesive must be moisture vapor permeable at the molecular level.

In accordance with the present invention, a moisture vapor permeable sheet material which is continuous and can be made optionally microporous, is provided which has moisture vapor permeability in its truest sense and which can also include an adhesive which is also continuous and moisture vapor permeable.

In addition to being moisture vapor permeable, one of the constituents of the dressing also provides desirable effects upon wound healing.

BRIEF DESCRIPTION OF THE INVENTION

A moisture vapor permeable sheet material is comprised of a homogeneous admixture of a synthetic polymeric material and a protein derivative. The sheet material is moisture vapor permeable and nonpenetrable by liquid water. The sheet material additionally can have coated thereon a pressure sensitive adhesive which is comprised of the synthetic organic polymer adhesive and a soluble protein derivative in solid solution. Sheet material is formed by providing a homogeneous fluid solution or admixture of a protein derivative and a synthetic organic polymer in a solvent. The protein derivative has a pH level compatible with the pH level of the organic polymer. A film is formed friom the homogeneous fluid admixture and the solvent or water is removed from the film to form the sheet material which is moisture vapor permeable. When the sheet material includes an adhesive, the adhesive is coated as a fluid solution in a solvent on one side of the sheet material. Solvents for the adhesive include water.

DETAILED DESCRIPTION OF THE INVENTION

"Protein derivative", as used herein, means and refers to materials which are derived from natural mammalian and reptilian proteins and which have been altered by hydrolysis or other types of severing of intermolecular and intramolecular bonds to provide an organic solvent soluble or water soluble product. Native insoluble protein may be used in the base sheet material. More particularly, soluble protein derivatives derived from collagen and elastin are preferred in the practice of the invention. Most preferably the soluble protein derivatives are derived from collagen and elastin and, more particularly, collagen and elastin derived from bovine hides and bovine parts. Soluble protein derivatives are in contrast to natural insoluble collagen which refers to collagen which cannot be dissolved in an aqueous alkaline or in any inorganic solution without chemical modification and includes hides, splits and other mammalian or reptilian coverings. More particularly, the collagen derivatives useful in the practice of the invention are preferably prepared from the corium which is the intermediate layer of the bovine hide between the grain and the flesh sides.

The elastin derivatives useful in the practice of the invention are those which are derived from elastin extracted from the bovine neck tendon which is recognized as being rich in elastin. Such elastin materials are exemplified by those disclosed in U.S. patent application Ser. No. 296,985, filed Aug. 27, 1981 of Gheorghe Cioca entitled "Partially Hydrolyzed Elastin from Limed Hide Trimmings", now U.S. Pat. No. 4,363,760, issued Dec. 14, 1982. Typically, these elastin derivatives have a molecular weight of below 1,000 and are soluble in water and various organic solvents. This patent application is incorporated herein by reference and made a part hereof.

The collagen derivatives useful in the practice of the invention are preferably those collagen derivatives which are soluble in water or organic solvent and are of relatively high molecular weight. Among the preferred collagen derivatives are those disclosed in U.S. Pat. No. 4,279,812 incorporated herein by reference, which describes a macromolecular reconstituted collagen having an average molecular weight of about 383,000 to 460,000 along with peptide chains up to 1,500,000. It is recognized that macromolecular biologically active collagen of this type is helpful in healing wounds and burns.

Another type of collagen derivative which is useful in the practice of the invention is oligopeptides derived from collagen such as is disclosed in U.S. Pat. No. 4,285,986 incorporated herein by reference and made a part hereof. This collagen derivative is prepared by heating natural insoluble collagen under heat and pressure in the presence of water to hydrolyze polypeptide chains to form oligopeptides having a molecular weight of between 5,000 and 20,000.

Yet another type of collagen derivative useful in the practice of the invention are soluble collagen fibers which have been reconstituted. Such soluble collagen fibers are more fully described in "Method of Preparing Soluble Collagen Fibers" which has been assigned U.S. Pat. No. 4,295,894 incorporated herein by reference and made a part hereof.

In addition to those types of collagen derivatives which have been mentioned herein, other types of collagen derivatives are useful so long as they exhibit solubility in organic solvents or water and are hydrophilic in nature.

Preferably, 1 to 15 percent by weight of the protein derivative is incorporated into the sheet material and preferably about 3 to 5 percent by weight of the protein derivative is incorporated into the material both based upon the total weight of the sheet material.

The synthetic polymeric material useful in the practice of the invention is selected from those synthetic polymeric materials which exhibit sufficient tensile strength and flexibility sufficient for bandaging material. Preferably, the minimum tensile strength of the sheet material is about 1,000 lbs./sq. inch, more preferably, at least 2,000 lbs./sq. inch and, most preferably, 4,000 lbs./sq. inch. Additionally, it is desired that the polymer impart a percent elongation of at least 30 percent to break.

Although polyacrylates, polyamides, polyolefins, polyvinyl halides and the like may be used as a synthetic polymeric material, it is preferred that thermoplastic polyurethane polymers be used as the synthetic polymeric material since these polymers have the desired tensile and elongation required for the final product. It is to be recognized that it is unnecessary for the synthetic polymeric material to exhibit moisture vapor permeability since the protein derivative incorporated into the sheet material provides this property. Therefore, a wide range of polymers, both polar and nonpolar, may be used in preparing the sheet material.

The polyurethanes useful in the practice of the invention may either be organic solvent based polyurethanes or polyurethanes which have been dissolved, dispersed or emulsified in an aqueous solution. Additionally, the polyurethanes useful in the practice of the invention are typically high performance thermoplastic polyurethanes which are soluble only in strong organic solvents such as dimethylformamide and the like.

The polyurethane polymers useful in the practice of the invention more particularly involve the reaction of a di or a polyisocyanate and compounds with multiple reactive hydrogens suitable for the preparation of polyurethanes. Such diisocyanates and reactive hydrogen compounds are more fully disclosed in U.S. Pat. Nos. 3,412,034 and 4,046,729. Further, the processes to prepare such polyurethanes are well recognized as exemplified by the aforementioned patents. In accordance with the present invention, aromatic, aliphatic and cycloaliphatic diisocyanates or mixtures thereof can be used in forming the polymer. Such diisocyanates, for example, are toluene 2-4 diisocyanate, toluene 2-6 diisocyanate, meta-phenylene diisocyanate, biphenylene 4-4'-diisocyanate, methylene-bis (4-phenyl isocyanate), 4-chloro-1, 3 phenylene diisocyanate, naphthylene-1, 5-diisocyanate, tetramethylene-1, 4-diisocyanate, hexamethylene-1, 6-diisocyanate, decamethylene-1, 10-diisocyanate, cyclohexylene-1, 4-diisocyanate, methylene-bis (4-cyclohexyl isocyanate), tetrahydronaphthylene diisocyanate, isophorone diisocyanate and the like. Preferably, the arylene diisocyanates are used most advantageously in the practice of the invention since they provide products whch have the required tensile strength for the final wound dressing. Characteristically, the arylene diisocyanates encompass those in which the isocyanate group is attached to the aromatic ring. The most preferred isocyanates are the 2-4 and 2-6 isomers of toluene diisocyanate and mixtures thereof due to their ready availability and their reactivity.

Selection of the aromatic or aliphatic diisocyanates is predicated upon the final end use of the particular material. It is well recognized by those skilled in the art that the aromatic isocyanates may be used where the final product is not excessively exposed to ultraviolet radiation which tends to yellow such polymeric compositions whereas the aliphatic diisocyanates may be more advantageously used in clear compositions such as surgical drapes and the like where transparency is necessary. Although these principles form a general basis for the particular isocyanate to be used, the aromatic diisocyanates may be further stabilized by well known ultraviolet stabilizers to enhance the final properties of the moisture vapor permeable sheet material. In addition, antioxidants may be added in art recognized levels to improve the characteristics of the final product. Typical antioxidants are the thioethers and phenolic antioxidants such as 4,4'-butylidine bis-meta-cresol and 2,6-ditert-butylpara-cresol.

The isocyanate is reacted with the multiple reactive hydrogen compounds such as diols, diamines or triols. In the case of diols or triols, they are typically either polyalkylene ether or polyester polyols. The polyalkylene ether polyol is the preferred active hydrogen containing polymeric material for formation of the polyurethane.

Polyether polyols, polyester polyols and other types of polyglycols may be used in forming the polyurethane in order to obtain the requisite final properties for the sheet material.

If it is desired to make the moisture vapor permeable sheet material from an aqueous system, the polyurethane may be emulsified with emulsifiers well recognized by those skilled in the art or a carboxylic acid group can be covalently bonded into the polymer backbone. Neutralization of the carboxyl groups in the polymer backbone with an amine, preferably a water soluble monoamine, affords water dilutability. Such techniques for providing water dilutable polyurethanes of sufficient molecular weight to provide the necessary physical properties to the moisture vapor permeable sheet material are more fully disclosed in U.S. Pat. No. 4,171,391 incorporated herein by reference.

When an adhesive is applied to the synthetic polymeric material and protein derivative solid solution, a pressure sensitive adhesive is preferred. The pressure sensitive adhesives useful in the practice of the invention can be those which are either solvent based or water based. Preferably, water based adhesives are most preferred since they will contact the skin and the wound and, therefore, must be necessarily of the lowest toxicity possible.

These adhesive compositions are typically acrylic adhesives having incorporated therein 1 to 15 percent by weight of protein derivatives. The protein derivatives useful in the adhesive are the same as those useful in the synthetic polymeric material.

In forming the moisture vapor permeable sheet material in accordance with the invention, an initial solvent or aqueous liquid solution or dispersion of the polymeric material and the protein is prepared. In the case of an organic solvent based solution, the synthetic polymer is dissolved in a suitable solvent. The solvent for the polyurethane must also act as a solvent or dispersing agent for the protein derivative. The solvent concentration for the liquid protein/polymer solution is adjusted in order to provide the appropriate rheological properties to form a film to provide the desired final thickness for the sheet material. Since the polyurethanes are preferably high performance polyurethanes, they must be dissolved in a strong solvent such as dimethylformamide. Dimethylformamide will also disperse protein derivatives such as the collagen fibers, the oligopeptides and the macromolecular biologically active collagen previously discussed. Such protein derivatives are soluble in dimethylsulfoxide, formamide, propyleneglycol and dipropyleneglycol. These solvents for the protein derivative are readily soluble along with the protein in the polyurethane solution. Thus, the appropriate concentration of polyurethane is dissolved in dimethylformamide and a concentrated solution or dispersion of the protein is added to the polyurethane solution to provide a liquid soluton of the protein and the polyurethane. Care must be taken that the pH of the protein derivative is adjusted so as to be compatible with the acidity or basicity of the polymer. Thus, in the case of solvent based polyurethane polymers, their pH is about neutral and, therefore, the pH of the protein derivative must be adjusted to between about 7 and 8.

After the liquid solution is formed, it is cast into film of the desired thickness in order to provide a sheet of a solid solution of synthetic polymeric material and protein derivative at a thickness of about 0.5 to about 5 mils. The film thickness is only limited by the final desired tensile and elongation properties and other desired physical properties since the moisture vapor permeability of the material remains the same regardless of the thickness of the sheet due to the true moisture vapor permeable nature of the composition which is continuous and nonmicroporous. The film may be formed by knife over roll film casting techniques or other similar techniques known to those skilled in the art. The solution is cast on a carrier paper which is a release paper that does not adhere substantially to the polymer protein composition. The film is dried at the temperature necessary to volatilize the solvent and thus provide the continuous nonmicroporous solid solution which constitutes the moisture vapor permeable sheet material.

After the sheet material has been formed, it can be overcoated with the adhesive, if desired. In the case of a solvent based polyurethane, the sheet can be directly overcoated with an aqueous adhesive by knife over roll, gravure, reverse roll coating or the like since the aqueous adhesive system will not attack the polyurethane sheet. Typically, the adhesive when in aqueous form is an aqueous acrylic emulsion having a solids content of about 40 to 65 percent by weight, a viscosity of 550 to 2,000 centipoise and a pH of 4 to 4.5. Incorporated into the adhesive is the desired protein derivative at the level of 1 to 15 percent and preferably 3 to 5 percent. Since this is an aqueous system, the protein derivative is provided in an aqueous solution or water compatible solvent system with the pH of the protein derivative adjusted to be compatible with the adhesive. Thus, if the pH of the adhesive is 4 to 4.5, the pH of the protein derivative should be adjusted likewise. The typical performance properties of the protein containing adhesive are 180° peel, Mylar/SS (PIW) 20 minute bond time, 2.0 to 4, 24 hour bond time, 6 to 8.

When polyurethane aqueous dispersions are used as the synthetic polymeric material for forming the moisture vapor permeable sheet material, the protein is incorporated again with the pH adjusted to be compatible with the polyurethane dispersion at the level of 1 to 15 percent by weight and preferably 3 to 5 percent by weight. These polyurethane protein compositions are more advantageously formed by using the macromolecular biologically active collagen since it adds viscosity to these dispersions allowing excellent regulation of film thickness for casting. The soluble collagen fibers and the oligopeptides derived from collagen and also the elastin may also be incorporated into the aqueous polyurethanes in order to form aqueous solutions or dispersions which can be cast as films. One particularly useful method of increasing moisture vapor permeability is by utilizing the macromolecular biologically active collagen. While the macromolecular biologically active collagen provides moisture vapor permeability due to its proteinaceous nature, the moisture vapor permeability can be enhanced when using macromolecular biologically active collagen by denaturing the collagen in situ during sheet formation. In order to provide this microporosity, the film of polymer and protein solution is cast and heated to evaporate the water and thus form the solid solution of biologically active collagen and the solid solution of biologically active collagen and polymer. Upon further heating, the biologically active collagen denatures and this denaturization causes a reorientation of the collagen molecule which in turn causes void spaces within the sheet material and thus microporosity.

Another method of providing microporosity to the sheet material is by incorporating into the liquid polymer protein dispersion or solution to be cast as a film sublimable salt such as ammonium chloride or the like. When these salts are incorporated at a level of 1 to 3 percent based upon the weight of the final sheet material, they will cause sufficient voids to increase the moisture vapor permeability of the sheet material.

In forming a microporous product in accordance with this method, the protein and polymer liquid solution is formed and the desired amount of sublimable salt is incorporated therein. The film is dried and then heated to the sublimation point of the salt and the salt vaporizes, thus causing voids within the sheet material and hence microporosity.

The sheet material in accordance with the invention, whether adhesive coated or without adhesive coating, has been found to have a moisture vapor permeability of at least 300 and preferably 500 or greater dependent upon the amount of protein derivative incorporated into the sheet material. Pure reconstituted collagen film exhibits the moisture vapor permeability of about 2400 g/m$^2$/24 hours at 40° C. Thus, as the protein concentration is increased within the sheet material, the moisture vapor permeability increases.

Although aqueous adhesives are preferred, solvent based adhesives may also be used. However, the application of the adhesive to the base sheet material must be done in accordance with different techniques. This is necesssary since the solvent and solvent based adhesive will attack the polymeric protein solid solution causing substantial rheological problems. In order to use the solvent based adhesive system, the adhesive can be separately coated on an appropriate substrate and then transfer coated onto one side of the base sheet material. Techniques such as these are well known to those skilled in the art.

In any event, the final sheet material is preferably the base sheet coated with the adhesive. Most preferably, the moisture vapor permeable sheet of this construction is formed on a continuous basis with the base sheet first formed on a release paper and the adhesive coated thereover. After the moisture permeable sheet material is formed, it is then wound on a roll with the uncoated side of the release material contacting the adhesive when wound on the roll. Thus, the material may be unwound and cut into the desired configuration for use as surgical drapes, bandaging, wound dressings and the like. Another feature of the invention is that the release paper can be selected to have a greater affinity for either the adhesive or the base sheet. Thus, when the material is unwound from the roll, either the adhesive or the base sheet can be exposed so that a premasking effect is achieved.

The invention can be more fully understood although not intended to be limited by the following examples.

EXAMPLE I

To an appropriate vessel was charged 75 parts by weight of 100 percent solids aromatic isocyanate based thermoplastic polyurethane which exhibits a tensile strength of 3,300 psi, an elongation at break of 330 percent at a 1 mil film thickness. 25 parts by weight of dimethylformamide was charged to the vessel and a solution of the polyurethane in dimehtylformamide was formed. A 30 percent solution of soluble collagen fibers prepared in accordance with U.S. Pat. No. 4,295,894 in dimethylsulfoxide was charged to the vessel in order to yield a final protein polymer solid solution sheet material having 3 parts by weight protein per 100 parts solid sheet material. The homogeneous solution was cast knife over roll to provide a final thickness of 1 mil. The film was cast on a carrier release paper and dried at 300° F. for 2 minutes. After drying, this base sheet had a moisture vapor permeability of 600 g/m$^2$/24 hours. An adhesive sold under the trade name Gelva Multipolymer Emulsion RA-2405, which was an aqueous acrylic emulsion at 65 percent solids having a pH of 4 to 4.5 and a viscosity of 1,200 centipoise was admixed with oligopeptides with the 30 percent solution of oligopeptides derived from collagen prepared in accordance with Example I of U.S. Pat. No. 4,285,986. The pH of the oligopeptides was adjusted to 4.5. Sufficient oligopeptides were charged in order to provide a protein content of about 3 percent by weight. The adhesive was coated knife over roll on the base sheet material and dried at 225° F. for two minutes.

The sheet material was then wound on a roll with the adhesive contacting the uncoated side of the release paper. The final moisture vapor permeable sheet material had a moisture vapor permeability of about 600 g/m$^2$/24 hours. The material can be used as a wound dressing, incise drape or other similar material.

EXAMPLE II

Example I was repeated except that oligopeptides derived from collagen which were dissolved in dipropylene glycol at the 30 percent level were incorporated into the polyurethane film. The moisture vapor permeable sheet material in accordance with Example II had a moisture vapor permeability of greater than 600 g/m$^2$/24 hours at 40° C.

EXAMPLE III

Example I was repeated except that the collagen fibers which were prepared in accordance with U.S. Pat. No. 4,295,894 were incorporated into the base film and adhesive in place of the protein constituent. The moisture vapor permeable sheet material had a moisture vapor permeability of greater than 600 g/m$^2$/24 hours at 40° C.

The moisture vapor permeable sheet material in accordance with Examples I through III had tensile strengths greater than 2,000 psi and approaching 4,000 psi.

EXAMPLE IV

An aqueous polyurethane dispersion based upon 4,4' methylene-bis (cyclohexyl isocyanate), a polyoxypropylene diol having a molecular weight of about 1,000 and dimethyl propionic acid was formed and solubilized by the addition of N-ethylmorpholine. The aqueous ionic dispersion had a solids content of 50 percent. To this aqueous ionic dispersion having a pH of between 7 and 8 was charged macromolecular biologically active collagen at a level appropriate so that the final base film has a protein content of 3 percent. The protein polyurethane aqueous dispersion was cast as described in Example I and coated with adhesive as in Example I except that it was heated to form the base film at 110° C. for 2 minutes. The heating at 110° C. for 2 minutes denatured the collagen and provided microporosity to the sheet material. The final sheet material had a moisture vapor transmission of greater than 900 g/m$^2$/24 hours at 40° C.

In addition to the sheet material in accordance with the invention, it has been found that polyurethane foam having protein derivatives incorporated therein is also useful as a wound dressing and the like since the protein has an affinity for water and moisturizes the composition and is helpful in treating wounds.

In another aspect of the invention reconstituted collagen sheet having a backing of the moisture vapor permeable sheet in accordance with the invention may be applied directly to wounds imparting healing properties to the composite.

In accordance with the present invention, it has been shown that the sheet material which is the solid solution of the polyurethane protein has vastly improved moisture vapor permeability as a continuous film while maintaining tensile strength and the required physical properties needed in preparing surgical drapes, bandaging and the like. In addition, the process in accordance with the invention is an efficient and simple process especially where water based adhesives are used in forming products in accordance with the invention.

Thus, although the invention has been described with reference to particular materials and particular processes, it is only to be limited so far as is set forth in the accompanying claims.

We claim:

1. A moisture vapor permeable sheet material comprising: a homogeneous mixture of a synthetic polymeric material and a protein, said sheet material being moisture vapor permeable and nonpenetrable by liquid water, and said protein being selected from the group consisting of collagen and elastin and derivatives of collagen and elastin.

2. The sheet material of claim 1 having a thickness of up to 5 mils.

3. The sheet material of claim 1 wherein said synthetic polymeric material is a thermoplastic polyurethane polymer.

4. The sheet material of claim 1 wherein said soluble protein derivative is macromolecular biologically active collagen.

5. The sheet material of claim 1 which is nonmicroporous.

6. The sheet material of claim 1 wherein said admixture is a solid solution.

7. The sheet material of claim 6 wherein said solid solution is formed from a polyurethane polymer and protein derivative in an organic solvent.

8. The sheet material of claim 6 wherein said solid solution is formed from a polyurethane polymer and protein derivative in an aqueous medium.

9. The sheet material of claim 8 wherein said polyurethane polymer is in the form of an aqueous polyurethane dispersion.

10. The sheet material of claim 1 wherein said soluble protein derivative is oligopeptides derived from collagen.

11. The sheet material of claim 10 wherein said oligopeptides have a molecular weight between 5,000 and 20,000.

12. The sheet material of claim 1 wherein said protein derivative is denatured macromolecular collagen.

13. The sheet material of claim 12 which is microporous.

14. The sheet material of claim 1 having about 1 to 15 percent by weight protein derivative.

15. The sheet material of claim 14 having about 3 to 5 percent by weight protein derivative.

16. The sheet material of claim 1 having a moisture vapor permeability of at least 300 g/m$^2$/24 hours at 40° C.

17. The sheet material of claim 16 having a moisture vapor permeability of at least 500 g/m$^2$/24 hours at 40° C.

18. The sheet material of claim 1 having a tensile strength of at least 1,000 psi.

19. The sheet material of claim 18 having a tensile strength of at least 2,000 psi.

* * * * *

UNITED STATES PATENT AND TRADEMARK OFFICE
CERTIFICATE OF CORRECTION

PATENT NO. : 4,497,862

DATED : February 5, 1985

INVENTOR(S) : Gheorge Cioca et al.

It is certified that error appears in the above-identified patent and that said Letters Patent is hereby corrected as shown below:

Column 4 Line 29 "whch" should read —which—.

Column 5 Line 50 "soluton" should read —solution—.

Column 7 Line 57 "dimehtylformamide" should read —dimethylformamide—.

Claim 1 - Column 9 Line 20 "mixture" should read —admixture—.

Signed and Sealed this

Twenty-fifth Day of June 1985

[SEAL]

Attest:

DONALD J. QUIGG

Attesting Officer    Acting Commissioner of Patents and Trademarks